(12) United States Patent
Dhanaraj et al.

(10) Patent No.: US 7,749,204 B2
(45) Date of Patent: Jul. 6, 2010

(54) REINFORCED ABSORBABLE MULTILAYERED FABRIC FOR USE IN TISSUE REPAIR AND REGENERATION

(75) Inventors: Sridevi Dhanaraj, Raritan, NJ (US); Dhanuraj S. Shetty, Somerset, NJ (US); Hiep Do, Hillsborough, NJ (US); Sanyog Manohar Pendharkar, Anandnagar, Pune (IN)

(73) Assignee: Ethicon, Inc., Somerville, NJ (US)

( * ) Notice: Subject to any disclaimer, the term of this patent is extended or adjusted under 35 U.S.C. 154(b) by 34 days.

(21) Appl. No.: 11/252,176

(22) Filed: Oct. 17, 2005

(65) Prior Publication Data

US 2006/0084930 A1 Apr. 20, 2006

Related U.S. Application Data

(60) Provisional application No. 60/620,624, filed on Oct. 20, 2004.

(51) Int. Cl.
*A61F 13/00* (2006.01)
*A61F 13/02* (2006.01)

(52) U.S. Cl. ..................... 604/305; 604/307
(58) Field of Classification Search ................ 604/305, 604/307
See application file for complete search history.

(56) References Cited

U.S. PATENT DOCUMENTS

| | | | |
|---|---|---|---|
| 2,517,772 A | 8/1950 | Doub et al. | |
| 2,773,000 A | 12/1956 | Masci | |
| 2,914,444 A | 11/1959 | Smith | |
| 3,328,529 A | 6/1967 | Anderson | |
| 3,364,200 A | 1/1968 | Aston et al. | |
| 3,868,955 A | 3/1975 | Siragusa et al. | |
| 3,875,937 A | 4/1975 | Schmitt et al. | |
| 4,214,582 A | 7/1980 | Patel | |
| 4,289,824 A | 9/1981 | Smith | |
| 4,407,787 A | 10/1983 | Stemberger | |
| 4,534,349 A * | 8/1985 | Barrows ..................... | 606/152 |
| 4,543,410 A | 9/1985 | Cruz, Jr. | |
| 4,600,574 A | 7/1986 | Lindner | |
| 4,626,253 A | 12/1986 | Broadnax | |
| 4,752,466 A | 6/1988 | Saferstein et al. | |
| 4,840,626 A | 6/1989 | Linksy | |
| 4,882,162 A | 11/1989 | Ikada et al. | |
| 4,948,540 A | 8/1990 | Nigam | |
| 5,002,551 A | 3/1991 | Linsky et al. | |
| 5,007,916 A | 4/1991 | Linsky et al. | |
| 5,026,589 A | 6/1991 | Schechtman et al. | |
| 5,134,229 A | 7/1992 | Saferstein et al. | |
| 5,180,398 A | 1/1993 | Boardman et al. | |
| 5,393,594 A | 2/1995 | Koyfman et al. | |
| 5,409,703 A | 4/1995 | McAnalley et al. | |
| 5,593,441 A | 1/1997 | Lichtenstein et al. | |
| 5,643,596 A | 7/1997 | Pruss et al. | |
| 5,645,849 A | 7/1997 | Pruss et al. | |
| 5,683,794 A | 11/1997 | Wadsworth et al. | |
| 5,686,090 A | 11/1997 | Schilder et al. | |
| 5,795,584 A | 8/1998 | Totakura et al. | |
| 5,821,343 A | 10/1998 | Keogh | |
| 5,843,057 A | 12/1998 | McCormack | |
| 5,866,165 A | 2/1999 | Liu et al. | |
| 5,914,118 A | 6/1999 | Yamamura et al. | |
| 5,925,552 A | 7/1999 | Keogh et al. | |
| 5,945,319 A | 8/1999 | Keogh | |
| 6,017,741 A | 1/2000 | Keogh | |
| 6,165,217 A * | 12/2000 | Hayes ..................... | 623/11.11 |
| 6,214,808 B1 | 4/2001 | Soe et al. | |
| 6,261,679 B1 | 7/2001 | Chen et al. | |
| 6,306,424 B1 | 10/2001 | Vyakarnam et al. | |
| 6,333,029 B1 | 12/2001 | Vyakarnam et al. | |
| 6,365,149 B2 | 4/2002 | Vyakarnam et al. | |
| 6,500,777 B1 | 12/2002 | Wiseman et al. | |
| 6,649,162 B1 | 11/2003 | Biering et al. | |
| 6,762,336 B1 | 7/2004 | MacPhee et al. | |
| 2001/0025154 A1 | 9/2001 | Rapp | |
| 2002/0012693 A1 | 1/2002 | Diegelmann et al. | |
| 2002/0120348 A1 | 8/2002 | Melican et al. | |
| 2002/0173213 A1 | 11/2002 | Chu et al. | |
| 2003/0073663 A1 | 4/2003 | Wisemann et al. | |
| 2003/0171052 A1 | 9/2003 | Bansal et al. | |
| 2004/0001879 A1 | 1/2004 | Guo et al. | |

(Continued)

FOREIGN PATENT DOCUMENTS

CS 217243 B 12/1982

(Continued)

OTHER PUBLICATIONS

De Groot J.H. et al. "Meniscal Tissue Regeneration in Porous 50/50 Copoly(1-lactide/epsilon-caprolactone) Implants" Biomaterials, Elsevier Science Publishers BV., Barking, GB, vol. 18, No. 8, Apr. 1997, pp. 613-622 XP004058386.

(Continued)

*Primary Examiner*—Jacqueline F. Stephens
(74) *Attorney, Agent, or Firm*—Roberts Mlotkowski Safran & Cole, P.C.

(57) ABSTRACT

The present invention is directed to a method of using a multilayered fabric comprising a first absorbable nonwoven fabric and a second absorbable woven or knitted fabric in tissue repair and regeneration.

13 Claims, No Drawings

U.S. PATENT DOCUMENTS

| | | | |
|---|---|---|---|
| 2004/0005350 | A1 | 1/2004 | Looney et al. |
| 2004/0078077 | A1* | 4/2004 | Binette et al. ............ 623/13.17 |
| 2004/0101546 | A1 | 5/2004 | Gorman et al. |
| 2004/0101547 | A1 | 5/2004 | Pendharkar |
| 2004/0101548 | A1 | 5/2004 | Pendharkar |
| 2004/0120993 | A1 | 6/2004 | Zhang et al. |
| 2004/0193088 | A1 | 9/2004 | Looney et al. |
| 2004/0243043 | A1 | 12/2004 | McCarthy et al. |
| 2005/0123588 | A1 | 6/2005 | Zhu et al. |

FOREIGN PATENT DOCUMENTS

| | | |
|---|---|---|
| CS | 235108 B1 | 5/1985 |
| CS | 238016 B1 | 11/1985 |
| EP | 0109197 A | 5/1984 |
| EP | 0177064 A | 4/1986 |
| EP | 0216378 A2 | 4/1987 |
| EP | 0361842 A | 4/1990 |
| EP | 0372969 A | 6/1990 |
| EP | 0468114 A2 | 1/1992 |
| EP | 0338829 B | 8/1993 |
| EP | 0610731 A1 | 8/1994 |
| EP | 0636378 A | 2/1995 |
| EP | 0647734 A1 | 4/1995 |
| EP | 0815879 A | 1/1998 |
| EP | 0878179 A | 11/1998 |
| EP | 1172115 A1 | 1/2002 |
| EP | 1378255 A2 | 1/2004 |
| EP | 1400624 A | 3/2004 |
| EP | 1424086 A1 | 6/2004 |
| EP | 1424087 A1 | 6/2004 |
| EP | 1430911 A2 | 6/2004 |
| EP | 1462122 A | 9/2004 |
| EP | 1574229 A | 9/2005 |
| GB | 0942305 A | 11/1963 |
| GB | 983073 A | 2/1965 |
| GB | 2314840 A | 1/1998 |
| GB | 2314842 A | 1/1998 |
| GB | 2344519 A | 6/2000 |
| IN | 159332 | 5/1987 |
| JP | 6087225 A | 5/1985 |
| RU | 2146264 C1 | 3/2000 |
| RU | 2235539 C1 | 9/2004 |
| WO | WO 91/08726 A | 6/1991 |
| WO | WO 96/16643 A | 6/1996 |
| WO | WO 96/40033 A1 | 12/1996 |
| WO | WO 98/00180 A1 | 1/1998 |
| WO | WO 98/00446 A | 1/1998 |
| WO | WO 98/33479 A | 8/1998 |
| WO | WO 99/01166 A1 | 1/1999 |
| WO | WO 00/01166 A1 | 1/2000 |
| WO | WO 01/22059 A2 | 3/2001 |
| WO | WO 01/23653 A1 | 4/2001 |
| WO | WO 02/02155 A1 | 1/2002 |
| WO | WO 02/22059 A1 | 3/2002 |
| WO | WO 02/058750 A2 | 8/2002 |
| WO | WO 03/020191 A1 | 3/2003 |
| WO | WO 2006/044882 A2 | 4/2006 |

OTHER PUBLICATIONS

International Search Report dated May 24, 2006 for corresponding Appln. No. PCT/US2005/037402.

International Search Report dated Jun. 7, 2006 for corresponding Appln. No. PCT/US2006/037406.

Singh, Mainder et al., "Biosoluble Polymers for Drug Delivery", Makromol. Chem. 181, No. 12, pp. 2433-2439 (1980).

Matras, H., "Fibrin Seal: The State of the Art", Journal of Oral Maxillofac Surg., vol. 43, No. 8, pp. 605-611 (1985).

Singh, M., et al., "An insulin delivery system from oxidized cellulose", Journal of Biomedical Materials Research, vol. 15, pp. 655-661 (1981).

Sinha, T.J.M., et al., "Blood-Cellulosics Interactions", Biomat. Med. Dev. Art. Org., No. 12(3-4), pp. 273-287 (1984-1985).

Stilwell, R.L., et al., "15. Oxidized Cellulose: Chemistry, Processing and Medical Applications", Handbook of Biodegradable Polymers, Edited by Domb et al., pp. 291-306 (1997).

Turaev, A.S., et al., "Hemostatic Activity and Reabsorbability of Carboxymethyl Cellulose", Khim.-Farm. Zh., 24(8), pp. 47-51 (1990 (English Abstract).

Frantz, V.K., et al., "Oxidized Cellulose-Absorbable Gauze (Cellulosic Acid)", Journal of American Medical Association, vol. 129 pp. 798-801 (1945).

Frantz, V.K., "New Absorbable Hemostatic Agents", The Bulletin, vol. 22, pp. 102-110 (1946).

Jackson, E.L., et al., "Application of the Cleavage Type of Oxidation by Periodic Acid to Starch and Cellulose", Journal of American Chemistry Society, vol. 59, pp. 2049-2050 (1937).

Lucas, O.N., "Inactivation of Thrombin by Oxidized Cellulose", Journal of Oral Therapeutics and Pharmacology, vol. 3, No. 4, pp. 262-268 (1967).

Arand, A.G. et al., "Intraoperative Chemical Hemostasis in Neurosurgery", Neurosurgery, vol. 18, No. 2, pp. 223-233 (1986).

ASTM (American Society for Testing and Materials), Designation: E11-87, "Standard Specification for Wire-Cloth Sieves for Testing Purposes" pp. 13-16 (1987).

Edwards, J.V., et al., "Modified cotton gauze dressing that selectively absorb neutrophil elastase activity in solution", Wound Repair and Regeneration, vol. 9, No. 1, pp. 50-58, (2001).

Davidson, G. F., "7-The Properties of the Oxycelluloses Formed in the Early Stages of the Oxidation of Cotton Cellulose by Periodic Acid and Metaperiodate", The Journal of the Textile Institute—Transactions, pp. T81-T96 (Jul. 1940).

Hercules Aqualon® Sodium Carboxmethylcellulose Product Specifications No. 4116-4, 1997.

Hercules Aqualon® Sodium Carboxmethylcellulose Physical and Chemical Properties 1995.

U.S. Appl. No. 11/252,175, filed Oct. 17, 2005, "Reinforced Absorbable Multilayered Hemostatic Wound Dressing", First named inventor Anne Jessica Gorman.

U.S. Appl. No. 11/400,849, filed Apr. 10, 2006, "Reinforced Absorbable Multilayered Hemostatic Wound Dressing", First named inventor Anne Jessica Gorman.

U.S. Appl. No. 11/252,120, filed Oct. 17, 2005, "Reinforced Absorbable Multilayered Fabric For Use In Medical Devices", First named inventor Dhanuraj S. Shetty.

Encyclopedia of Polymer Science and Engineering, vol. 10, (1997) pp. 204-253.

International Search Report dated Dec. 8, 2006 for corresponding Appln. No. PCT/US2006/013284.

* cited by examiner

REINFORCED ABSORBABLE MULTILAYERED FABRIC FOR USE IN TISSUE REPAIR AND REGENERATION This application claims priority from U.S. Provisional Application Ser. No. 60/620,624, filed on 20 Oct. 2004.

FIELD OF THE INVENTION

The present invention relates to a method for using a reinforced absorbable multilayered fabric in tissue repair and regeneration.

BACKGROUND OF THE INVENTION

It is generally know to use multilayered fabrics in connection with medical procedures. For example, multilayered fabrics are used as all purpose pads, wound dressings, surgical meshes, including hernia repair meshes, adhesion prevention meshes and tissue reinforcement meshes, defect closure devices, and hemostats.

For example, U.S. Pat. No. 5,593,441 to Lichtenstein et al describes a composite prosthesis preferably having a sheet of polypropylene mesh that allows tissue in-growth, such as Marlex® mesh. This reference discloses that other surgical materials that are suitable for tissue reinforcement and defect closure may be utilized, including absorbable meshes such as a polyglactin 910 (Vicryl®) mesh. The composite prosthesis of Lichtenstein et al also has an adhesion barrier, preferably a sheet of silicone elastomer. This reference generally suggests that that an oxidized regenerated cellulose such as Interceed® (TC7) absorbable adhesion barrier (commercially available from Ethicon, Inc., in Somerville, N.J.) may be used as the adhesion barrier to produce a composite prosthesis having short term effectiveness. The composite prosthesis of Lichtenstein et al is described for use in reinforcing and repairing a weakened muscular wall while limiting the incidence of postoperative adhesions.

U.S. Pat. No. 5,686,090 to Schilder et al describes the use of a fleece in combination with a nonabsorbable or absorbable film to prevent mis-growths to adjacent tissue and to reduce adhesions. Schilder et al generally discloses that polypropylene, polyester, polyglactin, polydioxanone or poligleca-prone 25 may be used as the fleece material or the film material. The term "fleece" as used in this reference is described by its porosity, which is described as being in the range between 100 and 1000 l/(m$^2$s) gas flow, measured with an inlet pressure of 200 Pa, a test surface of 50 cm$^2$ and a test thickness of 1 mm. The composite of Schilder et al is generally described as being a multilayered implant.

Additionally, multilayered fabrics are useful for tissue engineering and orthopedic applications. The recent emergence of tissue engineering offers numerous approaches to repair and regenerate damaged/diseased tissue. Tissue engineering strategies have explored the use of biomaterials in combination with cells and/or growth factors to develop biological substitutes that ultimately can restore or improve tissue function. The use of colonizable and remodelable scaffolding materials has been studied extensively as tissue templates, conduits, barriers, and reservoirs. In particular, synthetic and natural materials in the form of foams, sponges, gels, hydrogels, textiles, and nonwovens have been used in vitro and in vivo to reconstruct/regenerate biological tissue, as well as deliver chemotactic agents for inducing tissue growth. The different forms of scaffolds may be laminated to form a multilayered tissue engineering scaffold.

However, the prior art fails to describe or suggest a reinforced absorbable multilayered fabric having a first absorbable nonwoven fabric reinforced by a second absorbable woven or knitted fabric.

As used herein, the term "nonwoven fabric" includes, but is not limited to, bonded fabrics, formed fabrics, or engineered fabrics, that are manufactured by processes other than spinning, weaving or knitting. More specifically, the term "nonwoven fabric" refers to a porous, textile-like material, usually in flat sheet form, composed primarily or entirely of staple fibers assembled in a web, sheet or batt. The structure of the nonwoven fabric is based on the arrangement of, for example, staple fibers that are typically arranged more or less randomly. The tensile, stress-strain and tactile properties of the nonwoven fabric ordinarily stem from fiber to fiber friction created by entanglement and reinforcement of, for example, staple fibers, and/or from adhesive, chemical or physical bonding. Notwithstanding, the raw materials used to manufacture the nonwoven fabric may be yarns, scrims, netting, or filaments made by processes that include spinning, weaving or knitting.

SUMMARY OF THE INVENTION

The present invention is directed to a method of using a reinforced absorbable multilayered fabric comprising a first absorbable nonwoven fabric reinforced by a second absorbable woven or knitted fabric for tissue repair and regeneration. The method comprises first preparing a repair site for implantation, and then disposing the reinforced absorbable multilayered fabric at the site. The first absorbable nonwoven fabric comprises fibers comprising aliphatic polyester polymers, copolymers, or blends thereof; while the second absorbable woven or knitted fabric comprises oxidized regenerated cellulose fibers.

DETAILED DESCRIPTION OF THE INVENTION

The reinforced absorbable multilayered fabric generally comprises a nonwoven fabric and a reinforcement fabric. The reinforcement fabric provides a backing to which the nonwoven fabric may be attached, either directly or indirectly.

The nonwoven fabric functions as the first absorbable nonwoven fabric of the reinforced absorbable multilayered fabric described herein. The first absorbable nonwoven fabric is comprised of fibers comprising aliphatic polyester polymers, copolymers, or blends thereof. The aliphatic polyesters are typically synthesized in a ring opening polymerization of monomers include but are not limited to lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one).

Preferably, the first absorbable nonwoven fabric comprises a copolymer of glycolide and lactide, in an amount ranging from 70 to 95% by molar basis glycolide and the remainder lactide.

In an alternative embodiment, the first absorbable nonwoven fabric comprises fibers comprised of aliphatic polyester polymers, copolymers, or blends in combination with oxidized polysaccharide fibers.

Preferably, the nonwoven fabric is made by processes other than spinning, weaving or knitting. For example, the nonwoven fabric may be prepared from yarn, scrims, netting or filaments that have been made by processes that include spinning, weaving or knitting. The yarn, scrims, netting and/or filaments are crimped to enhance entanglement with each other and attachment to the second absorbable woven or knitted fabric. Such yarn, scrims, netting and/or filaments may be cut into staple that is long enough to entangle. The staple may be between about 0.1 and 3.0 inches long, preferably between about 0.75 and 2.5 inches, and most preferably between about 1.5 and 2.0 inches. The staple may be carded to create a nonwoven batt, which may be then needlepunched or calendared into the first absorbable nonwoven fabric. Additionally, the staple may be kinked or piled.

Other methods known for the production of nonwoven fabrics may be utilized and include such processes as air laying, wet forming and stitch bonding. Such procedures are generally discussed in the Encyclopedia of Polymer Science and Engineering, Vol. 10, pp. 204-253 (1987) and Introduction to Nonwovens by Albin Turbank (Tappi Press, Atlanta Ga. 1999), both incorporated herein in their entirety by reference.

The thickness of the nonwoven fabric may range from about 0.25 to 2 mm. The basis weight of the nonwoven fabric ranges from about 0.01 to 0.2 $g/in^2$; preferably from about 0.03 to 0.1 $g/in^2$; and most preferably from about 0.04 to 0.08 $g/in^2$. The weight percent of first absorbable nonwoven fabric may range from about 10 to 80 percent, based upon the total weight of the reinforced absorbable multilayered fabric.

The second absorbable woven or knitted fabric functions as the reinforcement fabric and comprises oxidized polysaccharides, in particular oxidized cellulose and the neutralized derivatives thereof. For example, the cellulose may be carboxylic-oxidized or aldehyde-oxidized cellulose. More preferably, oxidized regenerated polysaccharides including, but without limitation, oxidized regenerated cellulose may be used to prepare the second absorbable woven or knitted fabric. Regenerated cellulose is preferred due to its higher degree of uniformity versus cellulose that has not been regenerated. Regenerated cellulose and a detailed description of how to make oxidized regenerated cellulose is set forth in U.S. Pat. Nos. 3,364,200, 5,180,398, and 4,626,253, the contents each of which is hereby incorporated by reference as if set forth in its entirety.

Examples of fabrics that may be utilized as the reinforcement fabric include, but are not limited to, Interceed® absorbable adhesion barrier, Surgicel® absorbable hemostat; Surgicel Nu-Knit® absorbable hemostat; and Surgicel® Fibrillar absorbable hemostat; each available from Johnson & Johnson Wound Management Worldwide or Gynecare Worldwide, each a division of Ethicon, Inc., Somerville, N.J.

The reinforcement fabric utilized in the present invention may be woven or knitted, provided that the fabric possesses the physical properties necessary for use in contemplated applications. Such fabrics, for example, are described in U.S. Pat. Nos. 4,626,253, 5,002,551 and 5,007,916, the contents of which are hereby incorporated by reference herein as if set forth in its entirety. In preferred embodiments, the reinforcement fabric is a warp knitted tricot fabric constructed of bright rayon yarn that is subsequently oxidized to include carboxyl or aldehyde moieties in amounts effective to provide the fabrics with biodegradability.

In an alternative embodiment, the second absorbable woven or knitted fabric comprises oxidized polysaccharide fibers in combination with fibers comprised of aliphatic polyester polymers, copolymers, or blends thereof.

The second absorbable woven or knitted fabric preferably comprises oxidized regenerated cellulose and may have a basis weight ranging from about 0.001 to 0.2 $g/in^2$, preferably in the range of about 0.01 to 0.1 $g/in^2$, and most preferably in the range of about 0.04 to 0.07 $g/in^2$.

The first absorbable nonwoven fabric is attached to the second absorbable woven or knitted fabric, either directly or indirectly. For example, the nonwoven fabric may be incorporated into the second absorbable woven or knitted fabric via needlepunching, calendaring, embossing or hydroentanglement, or chemical or thermal bonding. The staple of the first absorbable nonwoven fabric may be entangled with each other and imbedded in the second absorbable woven or knitted fabric. More particularly, for methods other than chemical or thermal bonding, the first absorbable nonwoven fabric may be attached to the second absorbable woven or knitted fabric such that at least about 1% of the staple of the first absorbable nonwoven fabric are exposed on the other side of the second absorbable woven or knitted fabric, preferably about 10-20% and preferably no greater than about 50%. This ensures that the first absorbable nonwoven fabric and the second absorbable woven or knitted fabric remain joined and do not delaminate under normal handling conditions. The reinforced absorbable multilayered fabric is uniform such that substantially none of the second absorbable woven or knitted fabric is visibly devoid of coverage by the first absorbable nonwoven fabric.

One method of making the multilayered fabric described herein is by the following process. Absorbable polymer fibers, having a denier per fiber of about 1 to 4, may be consolidated to about 80 to 120 denier multifilament yarn and then to about 800 to 1200 denier yarns, thermally crimped and then cut to a staple having a length between about 0.75 and 2.5 inch. The staple may be fed into a multiroller dry lay carding machine one or more times and carded into a uniform nonwoven batt, while humidity is controlled between about 40-60% at a room temperature of 60 to 75° C. The batt may be further processed via needlepunching or any other means such as calendaring. Thereafter, the first absorbable nonwoven fabric may be attached to the second absorbable woven or knitted fabric by various techniques such as needlepunching. The reinforced absorbable multilayered fabric may then be scoured by washing in an appropriate solvent and dried under mild conditions for approximately 30 minutes.

It is desirable to control process parameters such as staple length, opening of the staple, staple feed rate, and relative humidity. For example, the consolidated yarns may have from about 5 to 50 crimps per inch and preferably from about 10 to 30 crimps per inch. Efficient cutting of the crimped yarns is desirable, as any long and incompletely cut staple tends to stick on the carding machine and cause pilling. A preferred range of the staple length is from about 0.75 to 2.5 inches, and preferably from about 1.5 to 2.0 inches.

To optimize uniformity and minimize the build-up of static electricity, the relative humidity may be controlled during batt processing, preferably during carding to form the uniform nonwoven batt. Preferably, the nonwoven batt is processed using a dry lay carding process at a relative humidity of at least about 40% at a room temperature of about 60 to 75° C. More preferably, the nonwoven batt is processed at a relative humidity of from about 50% to 60%.

The multilayered fabric is scoured using solvents suitable to dissolve any spin finish. Solvents include, but are not limited to, isopropyl alcohol, hexane, ethyl acetate, and methylene chloride. The multilayered fabric is then dried under conditions to provide sufficient drying while minimizing shrinkage.

The reinforced absorbable multilayered fabric may have an average thickness of between about 0.75 and 3.0 mm, preferably between about 1.00 and 2.5 mm, and most preferably between about 1.2 and 2.0 mm. The basis weight of the reinforced absorbable multilayered fabric is between about 0.05 and 0.25 $g/in^2$, preferably between about 0.08 and 0.2 $g/in^2$, and most preferably between about 0.1 and 0.18 $g/in^2$.

The reinforced absorbable multilayered fabric is uniform such that there is no more than about 10% variation (relative standard deviation of the mean) in the basis weight or thickness across each square inch of the.

Additionally, the reinforced absorbable multilayered fabric may contain bioactive agents to aid in the repair or regeneration of tissue. Examples of bioactive agents include cell attachment mediators, such as peptide-containing variations of the "RGD" integrin binding sequence known to affect cellular attachment, biologically active ligands, and substances that enhance or exclude particular varieties of cellular or tissue ingrowth. Examples of such substances include integrin binding sequence, ligands, bone morphogenic proteins, epidermal growth factor, IGF-I, IGF-II, TGF-β I-III, growth differentiation factor, parathyroid hormone, vascular endothelial growth factor, hyaluronic acid, glycoprotein, lipoprotein, bFGF, TGF-beta superfamily factors, BMP-2, BMP-4, BMP-6, BMP-12, sonic hedgehog, GDF5, GDF6, GDF8, PDGF, recombinant human growth and differentiation factor 5 (rhGDF-5), small molecules that affect the upregulation of specific growth factors, tenascin-C, fibronectin, thromboelastin, thrombin-derived peptides, heparin-binding domains, and the like.

Bioactive agents may also include biologically derived substance selected from the group consisting of demineralized bone matrix (DBM), platelet rich plasma, bone marrow aspirate and bone fragments, all of which may be from autogenic, allogenic, or xenogenic sources.

In other embodiments, the reinforced absorbable multilayered fabric may contain an inorganic filler. The inorganic filler may be selected from alpha-tricalcium phosphate, beta-tricalcium phosphate, calcium carbonate, barium carbonate, calcium sulfate, barium sulfate, hydroxyapatite, and mixtures thereof. In certain embodiments the inorganic filler comprises a polymorph of calcium phosphate such as a phosphate glass.

In yet another embodiment, the reinforced absorbable multilayered fabric can be seeded or cultured with appropriate cell types prior to implantation for the targeted tissue. Cells which can be seeded or cultured on the matrices of the current invention include, but are not limited to, bone marrow cells, stromal cells, stem cells, embryonic stem cells, chondrocytes, osteoblasts, osteocytes, osteoclasts, fibroblasts, pluripotent cells, chondrocyte progenitors, endothelial cells, macrophages, leukocytes, 5 adipocytes, monocytes, plasma cells, mast cells, umbilical cord cells, postpartum derived cells, mesenchymal stem cells, epithelial cells, myoblasts, and precursor cells derived from adipose tissue.

The cells can be seeded on the multilayered fabric for a short period of time, e.g. less than one day, just prior to implantation, or cultured for longer a period, e.g. greater than one day, to allow for cell proliferation and matrix synthesis within the seeded fabric prior to implantation.

The reinforced absorbable multilayered fabric can be used as a scaffold in tissue repair and regeneration applications. Examples of tissue repair and regeneration include rotator cuff repair, repair of damaged knee cartilage, and regeneration of skin, muscle, or bone lost due to disease or injury.

The method for using the reinforced absorbable multilayered fabric is to: first prepare a repair site for implantation, and then dispose the fabric at the site of repair. The fabric may be attached to the site of repair with sutures, tacks, or any of a number of biocompatible glues.

EXAMPLE 1

Nonwoven PGL Fabric with ORC Fabric

Poly (glycolide-co-lactide) (PGL, 90/10 mol/mol) was melt-spun into fiber. A multi-filament yarn was consolidated, crimped and cut into staple having a length of 1.75 inches. The staple was carded to create a nonwoven batt and then compacted to a thickness of about 1.25 mm and a density of about 98.1 mg/cc. The nonwoven fabric was then needlepunched into a knitted carboxylic-oxidized regenerated cellulose (ORC) fabric, available from Ethicon, Inc., under the tradename Interceed®, to secure the nonwoven fabric to the ORC fabric. The final multilayered fabric comprised about 60 weight percent of the nonwoven fabric.

EXAMPLE 2

Nonwoven PGL Fabric with ORC Fabric

Poly (glycolide-co-lactide) (PGL, 90/10 mol/mol) was melt-spun into fiber. A multi-filament yarn was consolidated, crimped and cut into staple having a length of 1.75 inches. The staple was carded to create a nonwoven batt and then compacted to a thickness of about 1.22 mm and a density of about 103.4 mg/cc. The nonwoven fabric was then needlepunched into a knitted carboxylic-oxidized regenerated cellulose fabric (ORC), available from Ethicon, Inc., under the tradename Surgicel NuKnit®, to secure the nonwoven fabric to the ORC fabric. The final multilayered fabric comprised about 25 weight percent of the nonwoven fabric.

EXAMPLE 3

Nonwoven PGL Fabric with ORC Fabric

Poly (glycolide-co-lactide) (PGL, 90/10 mol/mol) was melt-spun into fiber. A multi-filament yarn was consolidated, crimped and cut into staple having a length of 1.75 inches. The staple was carded to create a nonwoven batt and then compacted a felt having a thickness of about 1.1 mm and a density of about 102.8 mg/cc. The nonwoven fabric was then needlepunched into a knitted carboxylic-oxidized regenerated cellulose fabric (ORC), available from Ethicon, Inc., under the tradename Surgicel®, to secure the nonwoven fabric to the ORC fabric. The final multilayered fabric comprised about 60 weight percent of the nonwoven fabric.

EXAMPLE 4

Nonwoven PGL Fabric with ORC Fabric

Poly (glycolide-co-lactide) (PGL, 90/10 mol/mol) was melt-spun into fiber. A 80 denier multifilament yarn was consolidated into a 800 denier consolidated yarn. The consolidated yarn was crimped at approximately 110 degree C. The crimped yarn was cut into staple having a length of about 1.25" in length. 20 g of the crimped staple was accurately weighed and laid out uniformly on the feed conveyor belt of a multi-roller carding machine. The environmental conditions (temp: 70 deg F./55% RH) were controlled. The staple was then carded to create a nonwoven batt. The batt was removed from the pick-up roller and cut into 4 equal parts. These were re-fed into the carder perpendicular to the collection direction. After this second pass the batt was weighed (19.8 g: 99% fabric yield) and then compacted into a felt. The compact felt was precisely laid onto an ORC fabric and firmly attached via 2 passes in the needlepunching equipment. The multilayered fabric was trimmed and scoured in 3 discrete isopropyl alcohol baths to remove spin finish and any machine oils. The scoured multilayered fabric was dried in an oven at 70 degree C. for 30 minutes, cooled and weighed.

The "thickness" of the multilayered fabric was measured as described herein. The measurement tools were:
(1) Mitutoyo Absolute gauge Model number ID-C125EB [Code number—543-452B]. The 1" diameter foot was used on the gauge.
(2) A magnetic holder was used to lock in place and set the caliper up to the die platen.
(3) Two metal plates ~2.75"×2"×0.60", weighing between 40.8 g to 41.5 g [combined total of ~82.18 g].

The multilayered fabric was placed on a platen surface that is a smooth and machined surface. The two metal plates were placed on top of each other on the multilayered fabric and gently pressed at their corners to make sure the multilayered fabric is flat. The gauge foot was placed onto the top of the metal plates and was then re-lifted and re-placed, at which time a reading was made.

12—1"×1" pieces were die-cut from the scoured multilayered fabric and accurately weighed. The thickness of each 1"×1" piece was measured 4-5 times in different areas of the metal plate in order to obtain a reliable average. The weight and thickness of each piece is shown in Table 1. The values indicate that the coverage of both layers is similar in all directions.

TABLE 1

| | Sheet #1 | | Sheet #2 | |
|---|---|---|---|---|
| Sample # | Weight (g) | Thickness (mm) | Weight (g) | Thickness (mm) |
| 1 | .132 | 1.53 | .13 | 1.58 |
| 2 | .132 | 1.58 | .124 | 1.57 |
| 3 | .131 | 1.59 | .13 | 1.62 |
| 4 | .129 | 1.55 | .134 | 1.64 |
| 5 | .126 | 1.58 | .126 | 1.56 |
| 6 | .125 | 1.5 | .131 | 1.59 |
| 7 | .129 | 1.56 | .136 | 1.7 |
| 8 | .127 | 1.52 | .131 | 1.62 |
| 9 | .132 | 1.55 | .131 | 1.57 |
| 10 | .123 | 1.58 | .136 | 1.58 |
| 11 | .128 | 1.58 | .135 | 1.65 |
| 12 | .13 | 1.51 | .133 | 1.55 |
| Average | 0.1287 | 1.5525 | 0.1314 | 1.6025 |
| Std. Dev | 0.0029 | 0.031 | 0.0037 | 0.044 |
| CV (%) | 2.304 | 2.002 | 2.837 | 2.767 |

EXAMPLE 5

Rotator Cuff Repair Using Reinforced Absorbable Multilayered Fabric

In the case of a rotator cuff problem, the surgeon first looks at the extent of an injury using an arthroscope. Then, under general anesthesia, the patient undergoes open surgery to repair the tear.

After the anesthetic has been administered and the shoulder has been prepared, a cosmetic incision is made over the top front corner of the shoulder. This incision allows access to the seam between the front and middle parts of the deltoid muscle. Splitting this seam allows access to the rotator cuff without detaching or damaging the important deltoid muscle, which is responsible for a significant portion of the shoulder's power. All scar tissue is removed from the space beneath the deltoid and the acromion (part of the shoulder blade to which the deltoid attaches). Thickened bursa and the rough edges of the rotator cuff and humerus (upper arm bone) are also smoothed to make sure that they pass smoothly beneath the acromion and deltoid.

The edges of the cuff tendons are identified and the quality and quantity of the cuff tissue is determined. The goal of the repair is to reattach good quality tendon to the location on the arm bone from which it was torn. A groove or trough is fashioned in the normal attachment site for the cuff. To support the tendon and aid in healing, the surgeon sutures a patch of reinforced absorbable multilayered fabric into place over it. Sutures (lengths of surgical thread) draw the edge of the tendon securely into the groove to which it is to heal.

The surgeon then completes the surgery by closing the deltoid muscle and the skin incision. Over time, the body creates new tissue in the area that matches surrounding tissue. The body also absorbs the implanted patch in two to four months.

EXAMPLE 6

Knee Cartilage Repair Using Reinforced Absorbable Multilayered Fabric

First, the surgeon examines the knee through an arthroscope—a small device that allows the doctor to see into your knee joint. If a lesion is detected, a surgical procedure is performed.

After the anesthetic has been administered and the knee has been prepared, a cosmetic incision is made through the skin over the top front corner of the patella. First, the damaged cartilage is removed. The reinforced absorbable multilayered fabric is then implanted into the lesion. The fabric may be attached to the lesion site with sutures, tacks, or any of a number of biocompatible glues.

The surgeon then completes the surgery by closing the skin incision. Cartilage cells migrate into and multiply in the implanted fabric, and the cell/fabric implant intergrates with surrounding cartilage. With time, the cells will mature and fill-in the lesion with hyaline cartilage.

EXAMPLE 7

Tissue Repair Using Reinforced Absorbable Multilayered Fabric

Goat cartilage was harvested from femoral condyles of 1 to 1½ year old goat knees. A first set of 5-millimeter diameter discs were made from the cartilage using a punch. The cartilage discs were washed in phosphate buffered saline (PBS) containing antibiotic and antimycotics, then rinsed in PBS. Separately, a second set of 5-millimeter diameter discs were made from ORC/Polyglactin multilayered fabric formed as described in Example 1 and sterilized by Ethylene Oxide (EtO).

The fabric discs were placed in between two cartilage discs and bonded together with bovine fibrin glue. Constructs were implanted subcutaneously in SCID mice. Six weeks following implantation, samples were collected and processed for histology. Histological slides were assessed for repair tissue in the fabric discs by Hematoxylin/Eosin and Safranin O staining.

Results showed that cells had migrated into the scaffolds and formed new repair tissue. At this time point the repair tissue was fibrous in nature.

EXAMPLE 8

Tissue Repair Using Reinforced Absorbable Multilayered Fabric Having a Bioactive Agent Constructs for SCID implantation were prepared similar to that described for Example 9 with the exception that the ORC/Polyglactin composites were loaded with 2.5 micrograms of recombinant human growth and differentiation factor 5 (rhGDF-5) and lyophilized. Constructs were implanted in SCID mice and processed similar to Example 7. Histological slides were assessed for repair tissue in scaffolds by Hematoxylin/Eosin and Safranin O staining.

Results showed that cells had migrated into the scaffolds and formed new repair tissue. In the presence of the growth factor new cartilage like repair tissue was formed within the scaffolds. This repair tissue stained positive for Safranin O a stain specific for sulfated proteoglycans.

While the examples demonstrate certain embodiments of the invention, they are not to be interpreted as limiting the scope of the invention, but rather as contributing to a complete description of the invention. All reinforcement fabrics described in the examples below are the nonsterile materials of the corresponding commercial products referred by their tradenames.

We claim:

1. A method of tissue repair and regeneration, said method comprising: preparing a repair site for implantation, providing a reinforced absorbable multilayered fabric, said fabric comprising: a first absorbable nonwoven fabric comprising staple having a length from about 1.5 to 2 inches, and a second absorbable woven or knitted fabric, and disposing said fabric at said site.

2. The method of claim 1, where said reinforced absorbable multilayered fabric is attached to said site of repair with suture, tack, or biocompatible glue.

3. The method of claim 1, where said first absorbable nonwoven fabric of said multilayered fabric comprises fibers comprised of aliphatic polyester polymers or copolymers of one or more monomers selected from the group consisting of lactic acid, lactide (including L-, D-, meso and D, L mixtures), glycolic acid, glycolide, .epsilon.-caprolactone, p-dioxanone, and trimethylene carbonate.

4. The method of claim 3, where said first absorbable nonwoven fabric comprises glycolide/lactide copolymer.

5. The method of claim 3, where said second absorbable woven or knitted fabric of said multilayered fabric comprises oxidized polysaccharides.

6. The method of claim 5, where said second absorbable woven or knitted fabric comprises oxidized cellulose.

7. The method of claim 5, where said second absorbable woven or knitted fabric comprises oxidized regenerated cellulose.

8. The method of claim 1, where said first absorbable nonwoven fabric comprises glycolide/lactide copolymer, and said second absorbable woven or knitted fabric comprises oxidized regenerated cellulose.

9. The method of claim 1, where said staple is crimped.

10. The method of claim 1, where said staple is derived from fiber of about 1 to 4 denier per filament.

11. The method of claim 10, where said first absorbable nonwoven fabric has a basis weight of about 0.01 to 0.2 g/in.sup.2; and said second absorbable woven or knitted fabric has a basis weight of about 0.001 to 0.2 g/in.sup.2.

12. The method of claim 1, where said reinforced absorbable multilayered fabric further comprises a bioactive agent selected from the group consisting of integrin binding sequence, ligands, bone morphogenic proteins, epidermal growth factor, IGF-I, IGF-II, TGF-.beta. I-Ill, growth differentiation factor, parathyroid hormone, vascular endothelial growth factor, hyaluronic acid, glycoprotein, lipoprotein, bFGF, TGF-beta superfamily factors, BMP-2, BMP-4, BMP-6, BMP-12, sonic hedgehog, GDF5, GDF6, GDF8, PDGF, recombinant human growth and differentiation factor 5, tenascin-C, fibronectin, thromboelastin, thrombin-derived peptides, heparin-binding domains, demineralized bone matrix, platelet rich plasma, bone marrow aspirate, and bone fragments.

13. The method of claim 1, where said reinforced absorbable multilayered fabric further comprises cells selected from the group consisting of bone marrow cells, stromal cells, stem cells, embryonic stem cells, chondrocytes, osteoblasts, osteocytes, osteoclasts, fibroblasts, pluripotent cells, chondrocyte progenitors, endothelial cells, macrophages, leukocytes, 5 adipocytes, monocytes, plasma cells, mast cells, umbilical cord cells, postpartum derived cells, mesenchymal stem cells, epithelial cells, myoblasts, and precursor cells derived from adipose tissue.

* * * * *